United States Patent [19]

Thompson

[11] Patent Number: 5,582,985
[45] Date of Patent: Dec. 10, 1996

[54] DETECTION OF MYCOBACTERIA

[75] Inventor: Curtis T. Thompson, San Francisco, Calif.

[73] Assignee: The Regents of the University of California, Oakland, Calif.

[21] Appl. No.: 289,953

[22] Filed: Aug. 5, 1994

[51] Int. Cl.⁶ .................. C12Q 1/68; C12Q 1/70
[52] U.S. Cl. ........................................ 435/6; 435/5
[58] Field of Search ................... 435/5, 6, 77, 78, 435/810, 7.21

[56] References Cited

U.S. PATENT DOCUMENTS

| | | | |
|---|---|---|---|
| 4,888,278 | 12/1989 | Singer et al. | 435/6 |
| 5,225,324 | 7/1993 | McFadden et al. | 435/6 |

FOREIGN PATENT DOCUMENTS

| | | |
|---|---|---|
| 0497646 | 8/1992 | European Pat. Off. . |
| WO89/02934 | 4/1989 | WIPO . |
| 9010715 | 9/1990 | WIPO . |

OTHER PUBLICATIONS

Amann, R. I. et al., "Fluorescent–Oligonucleotide Probing of Whole Cells for Determinative, Phylogenetic, and Environmental Studies in Microbiology", J. Bacteriol. 172:762–770 (1990).

Bolmont, C. et al., "Desmin expression in fibroblasts of murine periovular granuloma during liver *Schistosoma mansoni* infection", Differentiation 46:89–95 (1991).

Braun–Howland, E. B. et al., "Development of a Rapid Method for Detecting Bacterial Cells In Situ Using 16S rRNA–Targeted Probes", BioTechniques 13:928–932 (1992).

deWit, P. E. J. et al., "In Situ Detection of Supernumerary Aberrations of Chromosome–Specific Repetitive DNA Targets in Interphase Nuclei in Human Melanoma Cell Lines and Tissue Sections", J. Invest. Dermatol. 98:450–458 (1992).

Distel, D. L. et al., "Phylogenetic Characterization and In Situ Localization of the Bacterial Symbiont of Shipworms (Teredinidae: Bivalvia) by Using 16S rRNA Sequence Analysis and Oligodeoxynucleotide Probe Hybridization", Applied and Environmental Microbiology 57:2376–2382 (1991).

Edwards, U. et al., Nucleic Acid. Res. 17:7843–7853 (1989).

Fain, J. S. et al., "Rapid Diagnosis of Legionella Infection by a Nonisotopic *In Situ* Hybridization Method", A.J.C.P. 95:719–723 (1991).

Gersdorf, H. et al., "Identification of *Bacteroides forsythus* in Subgingival Plaque from Patients with Advanced Periodontitis", J. Clin. Microbiol. 31:941–946 (1993).

Ghirardini, C. et al., "*Chlamydia trachomatis* Infections in Asymptomatic Women Results of a Study Employing Different Staining Techniques", Acta Cytologica, 33:115–119 (Jan.–Feb. 1989).

Gleaves, C. A. et al., "Direct Detection of Cytomegalovirus from Bronchoalveolar Lavage Samples by Using a Rapid In Situ DNA Hybridization Assay", J. Clin. Microbiol. 27:2429–2432, (1989).

Hahn, D. et al., "Detection of micro–organisms in soil after *in situ* hybridization with rRNA–targeted, fluorescently labelled oligonucleotides", J. General Microbiol. 138:879–887 (1992).

Jurtshuk, R. J. et al., "Rapid In Situ Hybridization Technique Using 16S rRNA Segments for Detecting and Differentiating the Closely Related Gram–Positive Organisms *Bacillus polymyxa* and *Bacillus macerans*", Appl. Environ. Microbiol. 58:2571–2578 (1992).

Kabnick, K. S. et al., "*In situ* analyses reveal that the two nuclei of *Giardia lamblia* are equivalent", J. Cell Sci. 95:353–360 (1990).

Miller, N. et al., "Evaluation of Gen–Probe Amplified Mycobacterium Tuberculosis Direct Test and PCR for Direct Detection of *Mycobacterium tuberculosis* in Clinical Specimens", J. Clin. Microbiol. 32:393–397 (1994).

Van Den Berg, F. M. et al., "Detection of Campylobacter pylori in stomach tissue by DNA in situ hybridization", J. Clin. Pathol. 42:995–1000 (1989).

Zarda, B. et al., "Identification of single bacterial cells using digoxigenin–labelled, rRNA–targeted oligonucleotides", J. General Microbiol. 137:2823–2830 (1991).

vanSoolingen, D., et al., "Occurence and Stability of Insertion Sequences in *Mycobacterium tuberculosis* Complex Strains: Evaluation of an Insertion Sequence–Dependent DNA Polymorphism as a Tool in the Epidemiology of Tuberculosis", Journal of Clinical Microbiology, vol. 29, No. 11, pp. 2578–2586, Nov. 1991.

Victor et al, J. Clin. Microbiol. 30:1514–1517 (1992).

Primary Examiner—Stephanie W. Zitomer
Assistant Examiner—Eggerton Campbell
Attorney, Agent, or Firm—Townsend and Townsend and Crew LLP

[57] ABSTRACT

The invention provides a method, compositions, and kits useful for detecting mycobacteria in a sample. The method includes contacting the sample with a formaldehyde solution, an organic solvent, and a protein-degrading agent prior to hybridizing a mycobacteria-specific nucleic acid probe to the sample. The invention has particular utility in detection and susceptibility screening of human-disease causing mycobacteria such as *Mycobacterium tuberculosis*.

31 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:1:

ATCGCCCGCA CGCTCACAGT TAAGCCGTGA GATTC     35

DETECTION OF MYCOBACTERIA

BACKGROUND OF THE INVENTION

Tuberculosis is the leading treatable infectious cause of death worldwide. A resurgence of tuberculosis has been observed in the United States since 1985, despite decades of public health efforts aimed at eradication. The causative agent in tuberculosis is *Mycobacterium tuberculosis* (MTb). Alarmingly, multiply drug resistant strains of *Mycobacterium tuberculosis* (MDRTb) have recently emerged and present a new and serious threat to health. In addition infection with another group of Mycobacteria, *Mycobacterium avium* complex (MAC) is a recent and dramatically growing health threat. MAC has been recognized to cause clinically significant disease in HIV-1 infected and other immunocompromised individuals. Disseminated MAC infection is estimated to be present in 17–28% of AIDS patients (Young, et al., *Rev. Infect. Dis.*, 8: 1024–1033 (1986)) and this is thought to be an underestimate since 47–53% of AIDs patients have MAC detected at autopsy (Wallace et al. *Chest*, 93:926–932 (1988)).

Diagnosis of pulmonary tuberculosis (Tb) has traditionally been based on a constellation of symptoms elicited by medical history and supported by an abnormal physical exam and chest x-ray, a positive tuberculin skin test reaction, observation of mycobacteria in patient derived specimens, clinical response to anti-mycobacterial therapy, and/or recovery of *Mycobacterium tuberculosis* (MTb) by culture. In contrast, because the clinical symptoms of MAC are nonspecific, diagnosis of MAC infection is dependent on the recovery of MAC from culture of patient-derived specimens by the clinical microbiology laboratory.

In the past, laboratory based detection of mycobacteria in a wide variety of patient-derived specimens has been limited to either: i) direct detection, or ii) recovery by microbiological culture. Direct detection by use of a variety of acid fast stains (i.e., Kinyoun, modified Kinyoun, Fite, auramine-rhodamine, etc.), has a number of disadvantages. First, the sensitivity of direct detection is estimated to be only 30%–75% when compared to the ability to recover mycobacteria from culture. Second, detection is highly dependent on the expertise of the observer and the amount of time spent examining the stained preparation. Third, if bacilli are detected by acid fast stains, species identification is not possible.

In contrast to direct detection methods, there have been significant advances over the past decade in optimizing culture systems for the recovery of mycobacteria. Use of radiometric culture systems has dramatically shortened the length of time necessary to recover mycobacteria to a minimum of 7 days (as compared to 2–6 weeks for nonradiometric mycobacterial culture systems). With radiometric culture systems, only an additional 7 days are required to determine antimicrobial susceptibility patterns (as compared with the 2–6 weeks required for traditional mycobacteria antimicrobial susceptibility testing). The development of commercially available chemiluminescent probes for species-specific DNA (based on MTb-unique 16S rRNA sequences) has dramatically shortened to 4 hours the time necessary for species typing once mycobacteria are recovered from culture (as compared to 2–4 weeks for traditional mycobacterial species typing using biochemical tests). Despite this progress, culture methods still require considerable time (i.e., the initial 7 days to recover the mycobacteria from culture) to yield results.

Newer technologies have recently been used to increase the sensitivity and decrease the subjectivity of direct detection methods. The polymerase chain reaction (PCR) has been intensely investigated as a method for direct detection of mycobacteria in respiratory specimens. Unfortunately, the technology, expertise, physical environment requirements, and reagent costs of performing PCR currently far outweigh those necessary for the performance and interpretation of an acid fast stained smear. Furthermore, at the present state of development, PCR tests result in an unacceptably high rate of false positive results for specimens lacking mycobacteria. (See, e.g., Noordhoek et al., *New Engl. J. Med.* 329:2036 (1993) and Noordhoek et al., *J. Clin. Microbiol.* 32:277–284 (1994)).

Thus, the existing methods for detection of Mycobacteria suffer from lack of reliability, technical difficulty, lack of sensitivity, or extended time periods required for culture. The resurgence of Tb and the emergence of MDRTb and MAC have emphasized the necessity for methods allowing rapid, accurate and convenient detection, species identification, and susceptibility testing of Mycobacteria.

SUMMARY OF THE INVENTION

The present invention provides a method for detecting mycobacteria in a sample comprising non-embedded animal cells or non-embedded bacteria. The method includes the following steps: treating the sample with a formaldehyde solution, contacting the sample with an organic solvent, contacting the sample with a protease or other protein-degrading agent, hybridizing a nucleic acid probe to the sample, wherein the probe specifically hybridizes to a Mycobacterium nucleic acid, and detecting the hybridized probe. The presence of the hybridization signal is indicative of the presence of mycobacteria in the sample. The method may further comprise treating the sample with a reducing agent before treatment with a protein-degrading agent.

The invention has particular use for diagnosis of infection by mycobacteria. The invention is also useful for determining efficacy of anti-mycobacterial drugs, and for susceptibility screening of mycobacteria isolates and strains. Preferred species of mycobacteria include *Mycobacterium tuberculosis* and *Mycobacterium avium* complex. The method is useful for detecting both intracellular and extracellular mycobacteria.

In a preferred embodiment, the sample may comprise sputum, blood, blood cells, a tissue biopsy sample, or pleural fluid, most preferably pleural fluid, blood, or sputum. In one embodiment the animal cells are mammalian cells, more preferably human cells and still more preferably mycobacterium-infectable cells, macrophages or macrophage-type cells. The animal cells may be grown in culture. Particularly preferred cultured cells include macrophages such as U937 cells and murine J cells.

The preferred formaldehyde containing solution is generally neutral buffered formalin. Preferred organic solvents include xylene, benzene or hexane, with xylene or hexane particularly preferred. Preferred protein-degrading agents include an acid or a protease, in particular a protease such as pepsin, pronase, lysozyme, trypsin, chymotrypsin, or proteinase K. In a preferred embodiment the sample is first treated with the protease at about between 0° C. and 10° C. and then treated with the protease at about between 15° C. and 60° C. When utilized, preferred reducing agents include sodium thiocyanate or guanidine thiocyanate. The nucleic acid probe may be about 15 to 100 bases long and more preferably is about 20 to 40 bases long. When the probe is made from RNA or genomic or cDNA it will preferably be about 100–600 bases in length, but may range up to about 2000 bases in length. Most preferably the probe comprises the total genomic DNA of a Mycobacterium. Labels for the nucleic acid probe include an enzyme, a radioisotope, biotin, digoxigenin, or a fluorophore, most preferably a fluorophore. Particularly preferred fluorophores (fluorescent labels) include fluorescein, Texas red, rhodamine, tetramethylrhodamine, Spectrum Orange (Imagenetics, Naperville, Ill.), Cy3 and Cy5. The fluorophore is easily detected using a fluorescence microscope. The hybridized mycobacteria nucleic acid may be RNA or DNA and in a preferred embodiment, the hybridized mycobacterial nucleic acid is DNA.

In a particularly preferred embodiment, the formaldehyde solution is neutral buffered formalin, the organic solvent is xylene, the protein degrading agent is pepsin, and the probe is fluorescently labeled total genomic DNA of *Mycobacterium tuberculosis*. Exposure to a protein-degrading agent may be preceded by exposure to sodium thiocyanate.

This invention also provides for an isolated nucleic acid probe capable of specifically hybridizing to a mycobacterial nucleic acid. In a preferred embodiment, the probe comprises the total genomic DNA of a Mycobacterium. Particularly preferred is the total genomic DNA of *Mycobacterium tuberculosis*. The probe is labeled and preferred labels include an enzyme, a radioisotope, biotin, digoxigenin, and a fluorophore. Particularly preferred fluorophores (fluorescent labels) include fluorescein, Texas red, rhodamine, tetramethylrhodamine, Spectrum Orange (Imagenetics, Naperville, Ill.), Cy3 and Cy5.

The invention also provides a kit for clinical detection of mycobacteria using the method of the present invention, as well as test samples useful as controls for the method. One such test sample or control consists of non-embedded animal cells having intracellular mycobacteria, where the cells are fixed with a solution comprising formaldehyde, and where a nucleic acid of the mycobacteria is hybridized to a labeled nucleic acid probe. In a preferred embodiment, the mycobacteria are of the species *Mycobacterium tuberculosis* or *Mycobacterium avium* complex. It is preferred that the probe is directly labeled with a fluorophore, however it may be indirectly labeled, for example through digoxigenin.

In one embodiment the kit comprises an instruction manual describing a method for detecting mycobacteria in a sample comprising non-embedded animal cells or non-embedded bacteria. The method includes the following steps: treating the sample with a formaldehyde solution, contacting the sample with an organic solvent, contacting the sample with a protease or other protein-degrading agent, hybridizing a nucleic add probe to the sample, wherein the probe specifically hybridizes to a Mycobacterium nucleic acid, and detecting the hybridized probe. The presence of the hybridization signal is indicative of the presence of mycobacteria in the sample. The kit may additionally include a test sample comprising a non-embedded animal cell having an intracellular mycobacterium, where the cell has been fixed with a solution comprising formaldehyde and where a nucleic acid of the mycobacterium is hybridized to a labeled nucleic acid probe. The kit may also include a container containing a labeled nucleic acid probe, a solution comprising formaldehyde, an organic solvent, a reducing agent, or a protease. Preferably the container will contain a nucleic acid probe more preferably the nucleic acid probe comprises the total genomic DNA of a Mycobacterium.

The method provided by the kit will preferably require neutral buffered formalin. Preferred organic solvents will include xylene, benzene or hexane, with xylene or hexane particularly preferred. Preferred protein-degrading agents include an acid or a protease, in particular a protease such as pepsin, pronase, lysozyme, trypsin, chymotrypsin, or proteinase K. In a preferred embodiment the method provided by the kit calls for the sample to be first treated with the protease at about between 0° C. and 10° C. and then treated with the protease at about between 15° C. and 60° C. When utilized, preferred reducing agents include sodium thiocyanate or guanidine thiocyanate. The nucleic acid probe may be about 15 to 100 bases long and more preferably is about 20 to 40 bases long. When the probe is made from RNA or genomic or cDNA it will preferably be about 100–600 bases in length, but may range up to about 2000 bases in length. Most preferably the probe comprises the total genomic DNA of a Mycobacterium. Labels for the nucleic acid probe include an enzyme, a radioisotope, biotin, digoxigenin, or a fluorophore, most preferably a fluorophore. Particularly preferred fluorophores (fluorescent labels) include fluorescein, Texas red, rhodamine, tetramethylrhodamine, Spectrum Orange (Imagenetics, Naperville, Ill.), Cy3 and Cy5. Any of these elements may be provided in the kit.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the term "mycobacteria" means any bacteria of the genera Mycobacterium (family Mycobacteriaceae, order Actinomycetales) and includes *Mycobacterium tuberculosis, Mycobacterium avium* complex, *Mycobacterium kansasii, Mycobacterium scrofulaceum, Mycobacterium bovis* and *Mycobacterium leprae*. These species and groups and others are described in Baron, S., ed. *Medical Microbiology*, 3rd Ed. (1991) Churchill Livingstone, N.Y., which is incorporated herein by reference.

The term "embedded" refers to a sample that has been infiltrated with a material to provide mechanical support and thereby reduce sample deformation during processes such as sectioning (preparing thin slices for viewing using a microscope). Embedding materials include waxes, such as paraffin wax, epoxies, gelatin, methacrylate, nitrocellulose various polymers and the like.

The term "non-embedded" refers to a sample that is not embedded, and was not previously embedded.

The term "organic solvent" includes aliphatic or aromatic hydrocarbon solvents including xylene, toluene, heptanes, octanes, benzene, acetone, acetonitrile and all isomers (e.g., ortho, meta, para) thereof.

The term "protein-degrading agent" refers to an agent that hydrolyses peptide bonds in proteins. Preferred protein degrading agents include proteases such as pepsin, trypsin, chymotrypsin, pronase, lysozyme, proteinase K, and the like. Protein degrading agents also include compounds such as cyanogen bromide (CNBr) and acids (e.g. HCl) and the like that also hydrolyze peptide bonds.

The term "sample" refers to a material with which bacteria may be associated. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. It will be recognized that the term "sample" also includes supernatant from cell cultures (which may contain free bacteria), cells from cell or tissue culture and other media in which it may be desirable to detect mycobacteria (e.g., food and water).

The term "susceptibility screening" refers to a process by which the susceptibility of bacteria to an antibiotic is determined by exposing to bacteria to an antibiotic treatment and determining the effect of the treatment on growth or viability of the bacteria.

The term "mycobacterium-infectable cell" refers to cells that can be infected by mycobacteria. Mycobacterium-infectable cells include macrophages, macrophage-type cells and other cell types which either under healthy or pathological conditions may engulf mycobacteria or be invaded by mycobacteria and thereby become infected.

The term "macrophage-type cells" refers to cells derived from blood monocytes that can engulf mycobacteria, or which mycobacteria can invade, including macrophages, Kupffer cells, histiocytes, microglial cells, alveolar macrophages, cell lines derived from macrophages and also including primary cell cultures or cell lines having the characteristic properties or markers of macrophages. As used herein, "macrophage-type cells" includes macrophages.

The term "intracellular", used in reference to mycobacteria, refers to a bacterium enclosed within a eukaryotic-cell membrane or within a vesicle in a cell. A mycobacterium that is not intracellular is "extracellular".

The term "reducing agent" refers to a compound capable of reducing a cystine bridge (i.e. a disulfide covalent bond between two cysteine amino acids or residues), to two cysteine thio side chains.

The term "nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

The terms "probe" or "nucleic acid probe" refer to a molecule which binds to a specific sequence or subsequence of a nucleic acid. A probe is preferably a nucleic acid which binds through complementary base pairing to the full sequence or to a subsequence of a target nucleic acid. It will be understood by one of skill in the art that probes may bind target sequences lacking complete complementarily with the probe sequence depending upon the stringency of the hybridization conditions. The probes are preferably directly labelled as with isotopes, chromophores, lumiphores, chromogens, or indirectly labelled such as with biotin to which a streptavidin complex may later bind. By assaying for the presence or absence of the probe, one can detect the presence or absence of the select sequence or subsequence.

A "label" is a composition detectable by spectroscopic, photochemical, biochemical, immunochemical, or chemical means. For example, useful labels include $^{32}P$, fluorescent dyes, electron-dense reagents, enzymes (as commonly used in an ELISA), biotin, dioxigenin, or haptens and proteins for which antisera or monoclonal antibodies are available.

A "labeled nucleic acid probe" is a nucleic acid probe that is bound, either covalently, through a linker, or through ionic, van der waals or hydrogen "bonds" to a label such that the presence of the probe may be detected by detecting the presence of the label bound to the probe.

The terms "isolated" or "biologically pure" refer to material which is substantially or essentially free from components which normally accompany it as found in its native state. The isolated nucleic acid probes of this invention do not contain materials normally associated with their in situ environment, in particular nuclear, cytosolic or membrane associated proteins or nucleic acids other than those nucleic acids intended to comprise the nucleic acid probe itself.

The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9M sodium chloride and 120 mM sodium citrate. Similarly, 0.2×SSC refers to a solution 0.2 times the SSC concentration or 0.03M sodium chloride and 4 mM sodium citrate.

The term "specifically hybridizes" is used to describe hybridization, through base-pair complementarity, of a probe to Mycobacterium nucleotide sequences, but not to nucleotide sequences of other organisms, including other bacteria, viruses, and eukaryotes (e.g. mammalian macrophage nucleotide sequences), that are present in a particular given sample under stringent hybridization and washing conditions. Stringent conditions will differ depending on the length and nature of the probe (i.e., RNA vs. DNA) and whether the hybridization is in situ hybridization or a Southern (or similar) hybridization. Typically in ex vivo hybridization (e.g. a Southern) both the wash and hybridization steps contribute to the "stringency" with the wash steps being particularly strong determinants of stringency. In contrast, in in situ hybridization, the hybridization conditions themselves determine effective "stringency" and considerable latitude can exist in the posthybridization washes without effecting stringency (see chapter 11 in *Hybridization with Nucleic Acid Probes*, Tijssen, ed., Elsevier, Amsterdam (1993)). The following stringent hybridization and washing conditions will be adequate to distinguish a specific probe (fluorescein-labeled) from a probe that is not specific in in situ hybridization: incubation of the probe with the sample for 12 hours at 37° C. in a solution containing denatured probe, 50% formamide, 2×SSC, and 10% (w/v) dextran sulfate, followed by washing in 1×SSC at 70° C. for 5 minutes; 2×SSC at 37° C. for 5 minutes; 2×SSC at room temperature for 5 minutes, and $H_2O$ at room temperature for 5 minutes. The following stringent hybridization and washing conditions will be adequate to distinguish a specific probe (when radiolabeled) from a probe that is not specific in a Southern hybridizaton: hybridization in a solution containing denatured probe and 5×SSC at 65° C. for 8–24 hours followed by 3 washes for 30 minutes each in 0.1×SSC, 0.1% SDS (sodium dodecyl sulfate) at 50°–65° C.

DETAILED DESCRIPTION

The present invention provides a method for detecting mycobacteria in a biological sample. Mycobacteria, as noted above, are the causative agents in tuberculosis, leprosy, and other diseases of humans and animals. The novel method of detection relies, in part, on the discovery that a protocol for in situ hybridization of non-embedded animals cells that utilizes a formaldehyde treatment, an exposure to organic solvent and a protein degradation agent results in highly specific labeling of mycobacteria with a relatively low background signal. The discovery that the method of this invention provides a high level of mycobacteria-specific labeling was unexpected. Mycobacteria are characterized by a complex cell wall containing mycolic acids, complex waxes, and unique glycolipids. This wall provides mycobacteria with extreme resistance to dehydration, acids and alkalis. In addition it appears to prevent penetration by nucleic acid probes thereby rendering in situ hybridization difficult. Generally hybridization with probes greater than 30 base pairs in length is unsuccessful. Even with shorter probes, specific labeling is often low (resulting in a low signal to noise [background] ratio) or often non-existent.

It was a particularly surprising discovery that an extremely high signal to background ratio was obtained with labeled mycobacteria when a reagent containing formaldehyde was used in fixation, but not when other methods of fixation known in the art are used. It was previously expected that the protein cross-linking induced by exposure to formalin would render the bacteria even more resistant to penetration by nucleic acid probes. See, for example, page 507 in *Hybridization with Nucleic Acid Probes,* Tijssen, ed., Elsevier, Amsterdam (1993) which states that precipitant fixatives are generally used for the detection of cellular DNA and indicates that formaldehyde "should be avoided whenever possible."

This high signal to background ratio permits easy detection of mycobacteria in samples in which the mycobacteria occur at low frequency thus facilitating detection of infection at early stages or in paucibacillary disease. Similarly the high signal strength results in a lower error rate and is amenable to automated detection methods. Additionally, the method of the present invention is simple to perform, highly reproducible, and utilizes reagents commonly found in clinical histology laboratories. It results in far more rapid screening than conventional methods requires less instrumentation and training than, for example, PCR, and is easily adapted for use with conventional automated tissue-processing instrumentation.

It will be appreciated that, in addition to its use as a diagnostic for disease states characterized by mycobacteria, the method of the present invention may also be used to screen for antibiotic resistance in mycobacteria and thereby identify an appropriate antibiotic treatment regimen. It is well known that numerous mycobacteria show varying degrees of antibiotic resistance. Consequently treatment of mycobacterial infections requires identifying antibiotics to which the particular strain of Mycobacterium is susceptible. This may be routinely accomplished by exposing cultured mycobacteria-infected cells to various treatments (e.g., antibiotic drugs) and then detecting the presence or absence of mycobacteria using the method of the present invention. The drug sensitivity of the mycobacteria is thereby determined. This determination is referred to as susceptibility screening. The sample, including a sample used in susceptibility testing, can include cells of a cell line used to culture mycobacteria. Most typically macrophages or macrophage-type cell lines are used.

For clarity, the method of the invention is described below in reference to samples in which mycobacteria are present. It will be apparent that the method is also used to ascertain that mycobacteria are not present in a sample. For instance, the absence of mycobacteria in a sample from a patient will indicate that the patient is not infected by mycobacteria, or that, e.g., in response to a drug treatment the patient has cleared the infection. Similarly, the absence of mycobacteria from cells exposed to an antibiotic or putative antibiotic in in vitro culture can indicate that the mycobacteria tested are susceptible to the drug used.

Sample Tissues and Cells

The method of the invention will be particularly useful in a clinical setting because it allows rapid and convenient screening of samples, such as specimens obtained from patients, for the presence of mycobacteria. The sample used will depend on the circumstances and judgment of the physician, but will typically be sputum, blood, blood cells (e.g., whim cells), tissue or fine needle biopsy samples, urine, peritoneal fluid, pleural fluid, or cells therefrom. Such material may be fresh (i.e., recently obtained) or may be frozen or otherwise preserved. It will be apparent that, in addition to the animal cells and mycobacteria, if present, the sample will contain other biological or non-biological components (e.g., mucous or extracellular material). Sputum, for example may also contain other microorganisms, especially bacteria or fungus, Streptococcus species (aerobic and anaerobic), Staphyloccus species, Hemophilus inf., Pseudomonas species, *E. coli,* Serratia, Proteus species, Candida and others.

Eukaryotic animal cells in cell-culture or tissue-culture or bacterial cells in culture are other examples of samples that may be screened for mycobacteria. Cell and tissue "culture" are terms of art that refer to growth in vitro of isolated eukaryotic cells, while bacterial culture refers to growing bacteria in a liquid or solid medium in the presence or absence of eukaryotic (e.g., host) cells in vitro. Preferred cells include mycobacterium-infectable cells, in particular alveolar macrophages obtained from bronchoalveolar lavage or peripheral blood macrophages. These cells may be obtained directly from a patient and cultured.

As used herein, the term "mycobacterium-infectable cells" refers to cells that can be infected by mycobacteria, including macrophages and macrophage-type cells. Mycobacterium-infectable cells may be easily identified by exposing the putative mycobacterium-infectable cell to mycobacteria and then utilizing the method of the present invention to detect the presence of intracellular mycobacteria. Preferred mycobacterium-infectable cells are "macrophage-type" cell lines including human U937 cells and Murine J cells. Other cell lines that can be infected by mycobacteria are available from private and commercial sources, such as American Type Culture Collection ("Catalogue of Cell Lines and Hybridomas," 6th edition (1988) Rockville, Md., U.S.A.); National Institute of General Medical Sciences 1990/1991 Catalog of Cell Lines (NIGMS) Human Genetic Mutant Cell Repository, Camden, N.J.; and ASHI Repository, Bingham and Women's Hospital, 75 Francis Street, Boston, Mass. 02115.

Methods of bacterial and cell culture are well known to those of skill in the art. For example, macrophages can be routinely cultured in DME supplemented with 5% newborn calf serum. Methods of macrophage culture are are well described by Freshney in *Culture of Animal Cells: A Manual of Basic Techniques.* Alan R. Lis, New York. (1983). Similarly, methods of mycobacterial culture are well known to those of skill in the art and can be found, for example in Good et al. *Clin. Chest Med.* 10: 315–322 (1984), *Heifets Ann. Rev. Respir. Dis.,* 137: 1217–1222 (1988), and Sommers et al. in *Color Atlas and Textbook of Diagnostic Microbiology, Third Edition,* J. B. Lippincott Co., Philadelphia, Pa. (1988) which are incorporated herein by reference).

While mycobacteria are typically invasive, i.e., able to survive and multiply within a host eukaryotic cell, they are also capable of surviving in the extracellular environment e.g., in sputum. See, e.g., *Medical Microbiology,* supra, at pages 139–142. Thus, another example of a sample suitable for the practice of this invention are samples that contain extracellular mycobacteria (e.g., sputum, blood, pleural fluid, bacteria isolated from culture, etc.).

While, in a preferred embodiment, the present invention is practiced with a non-embedded sample, the method is also suitable for practice with a biological sample that has been fixed in a manner compatible with the practice of the invention, as described in detail below, and embedded in a wax such as paraffin, or other material used to prepare tissues for sectioning if the embedding material is subsequently removed. Use of these samples according to the method of the invention will be useful for retroactive screening of archival samples from patients (i.e., samples collected and processed for histological examination).

Histochemical Preparation

The method of the instant invention includes the following steps: a) contacting the sample with a solution comprising formaldehyde; b) contacting the sample with an organic solvent; c) contacting the sample with a protein-degrading agent; d) hybridizing a labeled nucleic acid probe to the sample, wherein the probe specifically hybridizes to a mycobacterium nucleic acid; and, e) detecting the hybridized probe. Each of these steps will be discussed in some detail below.

A. Contacting the Sample with a Solution Comprising Formaldehyde

One step in the practice of the method is the exposure of the sample to a solution containing formaldehyde. This exposure causes the biological material in the sample to become fixed. As noted in the examples below, one element of this invention is the surprising discovery that mycobacteria can be easily detected using in situ hybridization when formaldehyde is used in fixation, but not when other methods of fixation known in the art are used.

The term "formaldehyde solution," as used herein, refers to an aqueous solution containing formaldehyde. Formaldehyde, HCHO, is a colorless gas usually marketed as a 37% w/w (equivalent to 40% w/v) aqueous solution usually called formalin. As used herein dilutions of formaldehyde will be designated in terms of the commercial product. Thus, for example, a 10% solution is 10 volumes of concentrated formalin (37% formaldehyde-saturated water) to 90 volumes of water. A formaldehyde solution can also be prepared by dissolving paraformaldehyde (a solid formaldehyde polymer), 4 g/100 ml for example, in distilled water and depolymerizing by heating to 80° C. to 90° C. for about 24 hours. A 1M solution of formaldehyde calls for 3 g of formaldehyde (HCHO) per 100 ml, whether derived from formalin or paraformaldehyde.

The formaldehyde-containing solution most commonly found in histology and pathology laboratories is formalin that additionally contains methanol (typically 8% to 15%) to reduce polymerization of the formaldehyde. Formalin, when reacting with protein, appears to form links between adjacent protein chains. The quantity of irreversibly bound protein drops as the pH of the solution rises above 10. For this reason, formalin reacts most efficiently as a buffered solution around the neutral point of pH 7.5–8.0. Addition of 4 g monohydrated acid sodium phosphate (or of the anhydrous acid potassium phosphate) and 6.5 g anhydrous disodium phosphate per liter gives approximately pH 7 and a total salt content of the two sodium salts of about 1%, dry weight. In a preferred embodiment, the formaldehyde solution comprises a solution buffered at about pH 6.0 to pH 9.0, more preferably pH 6.8 to pH 7.2 containing about 15% to 47% formalin (6% to 20% formaldehyde) more preferably about 18% to 28% formalin (8% to 12% formaldehyde).

In one embodiment the formaldehyde solution is buffered to a neutral pH (i.e., neutral-buffered). A preferred embodiment of the invention makes use of neutral-buffered formalin (i.e., formalin buffered to about neutral pH), with a most preferred embodiment comprising 10% neutral buffered formalin (approximately 3.7% formaldehyde).

The sample may be exposed to the formaldehyde solution, as well as other solutions (e.g., wash solutions, solvents, etc.) in a number of ways. The sample may be immersed in the formaldehyde solution before or after it is affixed to a supporting material (e.g., a slide). Most often the sample will be affixed to a glass or plastic slide after the exposure to the formaldehyde solution and immersed in the subsequent solutions. Alternatively, the solutions can be poured or pipetted over the sample. So long as the cells come into contact with the solutions, any convenient method is acceptable. Moreover, a glass slide is not essential; various other methods are suitable for exposing the sample to solutions. For example, all of the processing may be performed with unaffixed cells or, alternatively, the cells might be adhered to a petri dish or to wells in a culture plate and the like.

The sample may be affixed to a glass slide or other support using a number of methods well known to those of skill in the art. For example, in a preferred embodiment, cells are affixed to a slide by simply drying them on a slide that has been gelatinized. Typically, glass slides are cleaned with an acid wash, or by soaking in ethanolic KOH (10% potassium hydroxide) and rinsing in double-distilled water. After drying (e.g., air drying), the cleaned slides may be dipped in a gelatin solution (0.1% gelatin, 0.01% chromium potassium sulfate at 70° C.) and dried in a vertical position. The cells to be affixed are then are diluted to an appropriate concentration, spread on the slide and dried (e.g., air dried). Cells and bacteria may also be affixed directly to bare glass slides. This may be accomplished by suspending the sample on the slide in a solvent that evaporates rapidly (e.g., acetone) and allowing the solution to rapidly evaporate thereby depositing the sample on the glass. Alternatively, the sample may be attached by heat fixing in which the slide with the sample is briefly held over a heater or flame. Other methods of affixing the sample to the slide are well known to those of skill in the art and may be found in any histochemistry book.

The formalin fixation step may be carried out at a variety of temperatures ranging from about 4° C. to about 70° C. For example, the fixation may be carried out at about 55° C., but about 37° C. is preferred, and about 24° C. (room temperature) is most preferred. It will be recognized that where the biological sample (e.g., cells) are affixed to a solid support the fixation step may be performed before or after the cells are affixed.

The duration of the fixation step may also be varied. When 10% neutral buffered formalin is used at room temperature, the fixation step should be at least more than 15 minutes. Once the sample has been exposed to the formaldehyde solution, it may be stored in that solution, or in an other solution for a period of time, until it is convenient to proceed to the other steps.

While, in a preferred embodiment, the present invention is practiced in a non-embedded sample, the method of the invention is also useful for detecting mycobacteria in samples that have been fixed using a formaldehyde solution and embedded. The term "embedded", as used herein refers to the practice of infiltrating a sample, such as a tissue sample, with a material such as a wax (e.g., paraffin). Embedding is typically done to prepare a sample for histological sectioning. A sample that has been embedded with a material, that can be removed may be used for the instant method. Paraffin is easily removed in the course of the exposure of the sample to an organic solvent (e.g., xylene); samples embedded using different compounds may require different treatments to remove the material.

B. Contacting the Sample with an Organic Solvent

Following the exposure of the sample to formaldehyde, the sample is contacted with an organic solvent. Without intending to be bound by a particular mechanism, it is believed that the organic solvent removes hydrophobic constituents of the Mycobacterium cell wall thereby increasing its penetrability by the hybridization probe. The organic solvent of the invention includes aliphatic or aromatic hydrocarbon solvents including xylenes, toluene, heptanes, octanes, benzene, acetone, acetonitrile and all isomers (e.g., ortho, meta, para) thereof. Xylene, hexane and benzene are preferred solvents, with hexane and xylene most preferred. It is preferred that the sample be contacted with the solvent for at least 40 minutes (preferably one wash of 10 minutes and one of 30 minutes) at 24° C., but an extended incubation (e.g., >12 hours) is acceptable. In a less preferred embodiment the sample can be contacted with the solvent at an elevated temperature (e.g., 55° C.) and the exposure time may be reduced.

Typically, the sample will be "washed" between steps. "Washing" refers to contacting the sample with a solution to remove or dilute a compound introduced in a previous step (e.g., formaldehyde or xylene). Washing solutions are typically compounds that solubilize and/or rinse away some or all of the composition introduced in the previous step. Various washing solutions are well known to those of skill in the art and include, but are not limited to, water, alcohol, various buffers, and organic solvents. In a preferred embodiment, wash solutions are either SSC with or without formamide, water, or alcohol.

The sample may also be dehydrated between steps. "Dehydration" refers to the removal of water from the sample. Typically dehydration is accomplished by contacting a sample with a series of solutions of increasing concentration of a compound (e.g., ethanol) that will replace the water in the sample. In a preferred embodiment solutions of increasing concentration (e.g., 70, 80, 95 & 100% ethanol) are used to remove water from the sample. One of skill in the art will recognize that numerous variations are possible in washing and dehydrating steps. In one embodiment, the sample is dehydrated and washed between the fixation step and the addition of the organic solvent by sequential immersion in 70%, 80%, 95%, and 100% solutions of ethanol (in water), each for about 2 minutes.

C. Contacting the Sample with a Protein-degrading Agent

Also following the exposure to the formaldehyde solution, the method provides that the sample be exposed to a protein degrading agent. A preferred protein degrading agent is a protease. A non-specific protease is most preferred. Useful proteases include, but are not limited to, trypsin, chymotrypsin, pepsin, pronase, lysozyme, and proteinase K.

In one embodiment, the sample is first contacted with the protease at a low temperature (at which the protease is less active), and then warmed so that the protease is more active. This procedure is believed to allow more effective proteolysis. Without intending to be bound by a particular mechanism, it is believed that the addition of protease at low temperature allows penetration of the constituents of the sample with the protease in a relatively inactive form so that upon warming proteolysis occurs more uniformly throughout the sample. Accordingly, in a preferred embodiment, the sample is first treated with the protease at about between 0° C. and 10° C. and then treated with the protease at about between 15° C. and 60° C. In a most preferred embodiment pepsin is added to the sample at 4° C. and incubated for 5 minutes, and then the sample and protease are incubated together at 37° C. for about 5 minutes.

The duration of the proteolysis step may be reduced and the efficiency of the digestion increased by treatment with a reducing agent. Without being bound to a particular theory, it is believed that the function of the reducing agent is to reduce cystine bonds in the proteins of the sample. Reducing agents active in proteins are well known to those of skill in the art and include, but are not limited to, sodium thiocyanate, guanidine thiocyanate and beta-mercaptoethanol.

As an alternative to the use of a protease, other protein-degrading agents well known to those of skill in the art may be used. For example, acid (e.g., 0.2M HCl), cyanogen bromide, hydroxylamine, or N-Bromosuccinimide (NBS) may be used as the protein degrading agent. Means of effecting proteolysis are well known to those of skill in the art and are described by Croft in chapter 2 of *Introduction to Protein Sequence Analysis,* John Wiley & Sons, New York (1980) which is incorporated herein by reference.

D. Hybridizing with a Labeled Nucleic Acid Probe

After the sample has been prepared according to the steps provided above, mycobacteria present in the sample are detected by exposing the sample to a nucleic acid probe under conditions in which the probe specifically hybridizes to a mycobacterial nucleic acid.

The nucleic acid probe is an RNA or DNA polynucleotide or oligonucleotide, or their analogues. The probes may be single or double stranded nucleotide sequences. The probes of the invention may be synthesized enzymatically, using methods well known in the art (e.g., nick translation, primer extension, reverse transcription, the polymerase chain reaction, and others, see Celeda et al., *Bio/Techniques,* 12: 98–102 (1992), Feinberg et al., *Analyt. Biochem.,* 132: 6–13 (1983), and Wachter, et al., *Exp. Cell. Res.,* 184: 61–71 (1983) which are incorporated herein by reference) or chemically (e.g., by methods such as the phosphoramidite method described by Beaucage and Carruthers, *Tetrahedron Lett.* 22:1859–1862 (1981), or by the triester method according to Matteucci, et al., *J. Am. Chem. Soc.,* 103:3185 (1981), both incorporated herein by reference).

The probe must be of sufficient length to be able to form a stable duplex with a mycobacterial nucleic acid in the sample, i.e., at least about 15 nucleotides, and may be longer (e.g., at least about 50 or 100 bases in length). Often the probe will be more than about 100 bases in length. For example, when probe is prepared by nick-translation of mycobacterial DNA in the presence of labeled nucleotides the average probe length may be about 100–600 bases, however, the probe may be up to about 2000 bases in length and still work well.

As noted above, the probe will be capable of specific hybridization to a mycobacterial nucleic acid. Such "specific hybridization" occurs when a probe hybridizes to a mycobacteria nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, Sambrook, supra, *Current Protocols in Molecular Biology,* F. Ausubel et al., ed. Greene Publishing and Wiley-Interscience, New York (1987) [hereinafter referred to as Sambrook], *Methods in Enzymology* Vol. 152, Berger, S. and Kimmel, A. ed. Academic Press, New York (1987) or Tijssen, J. *Hybridization with Nucleic Acid Probes* pp. 495–524, Elsevier, Amsterdam (1993) all of which are incorporated herein by reference.

Usually, at least a pan of the probe will have considerable sequence identity with the target (i.e., mycobacterial) nucleic acid. Although the extent of the sequence identity required for specific hybridization will depend on the length of the probe and the hybridization conditions, the probe will usually have at least 70% identity to the mycobacteria nucleic acid, more usually at least 80% identity, still more usually at least 90% identity and most usually at least 95% identity.

The mycobacterial nucleic acid to which the probe hybridizes will typically be DNA, but can also be RNA (e.g., ribosomal or messenger RNA).

A probe can be identified as capable of hybridizing specifically to a mycobacterial nucleic acid by hybridizing the probe to a sample treated according the protocol of this invention where the sample contains both mycobacteria and animal cells (e.g., macrophages) and/or other bacteria. A probe is specific if the probe's characteristic signal is associated with mycobacteria in the sample and not generally with the animal cells, non-mycobacteria bacterial cells or non-biological materials (e.g., substrate) in a sample.

The following stringent in situ hybridization and washing conditions will be adequate to distinguish a specific probe (e.g., a fluorescently labeled DNA probe) from a probe that is not specific: incubation of the probe with the sample for 12 hours at 37° C. in a solution containing denatured probe, 50% formamide, 2×SSC, and 10% (w/v) dextran sulfate, followed by washing in 1×SSC at 70° C. for 5 minutes; 2×SSC at 37° C. for 5 minutes; 2×SSC at room temperature for 5 minutes, and $H_2O$ at room temperature for 5 minutes. Those of skill will be aware that it will often be advantageous in nucleic acid hybridizations (i.e., in situ, Southern, or other) to include detergents (e.g., sodium dodecyl sulfate), chelating agents (e.g., EDTA) or other reagents (e.g., buffers, Denhardt's solution, dextran sulfate) in the hybridization or wash solutions.

To test the specificity of a mycobacterial species-specific probe, the probe can be tested on cells (e.g., macrophages or J cells) containing bacteria of one species (e.g., MAC) and compared with the results from cells containing bacteria of another species (e.g., MTb). Similarly, hybridization to extracellular mycobacteria of one species may be compared to hybridization to extracellular bacteria of another species. In either case, if hybridization is observed only on mycobacteria of one species the probe will be identified as specifically distinguishing between the two species.

It will be apparent to those of ordinary skill in the art that a second convenient method for determining whether a probe is specific for a mycobacterial nucleic acid utilizes a Southern blot (or Dot blot) using DNA prepared from one or more species of mycobacteria. Briefly, to identify a probe specific for mycobacteria, DNA is isolated from the mycobacteria (e.g., as described in Example 1, infra) and from a second source (e.g., human cells and/or other bacteria, see Sambrook, supra). The DNA is digested with a restriction enzyme (e.g., EcoR1), size fractionated by electrophoresis through an agarose gel and transferred to a solid (e.g., charged nylon) matrix. Following denaturation and/or prehybridization steps known in the art, the probe is hybridized to the immobilized DNAs under stringent conditions. Stringent hybridization conditions will depend on the probe used and can be estimated from the calculated $T_m$ (melting temperature) of the hybridized probe (see, e.g., Sambrook for a description of calculation of the $T_m$). For radioactively-labeled DNA or RNA probes an example of stringent hybridization conditions is hybridization in a solution containing denatured probe and 5×SSC at 65° C. for 8–24 hours followed by washes in 0.1×SSC, 0.1% SDS (sodium dodecyl sulfate) at 50°–65° C. In general the temperature and salt concentration are chosen so that the post hybridization wash occurs at a temperature that is about 5° C. below the $T_M$ of the hybrid. Thus for a particular salt concentration the temperature may be selected that is 5° C. below the $T_M$ or conversely, for a particular temperature, the salt concentration is chosen to provide a $T_M$ for the hybrid that is 5° C. warmer than the wash temperature. Following stringent hybridization and washing, a probe that hybridizes to the mycobacterial DNA but not to the non-mycobacterial DNA, as evidenced by the presence of a signal associated with the mycobacteria and the absence of a signal from non-mycobacterial nucleic acids, is identified as specific for the mycobacteria.

Analogously, a probe can be identified as being specific for a species of mycobacteria by carrying out the Southern blot described, as described above, using DNA isolated from two species of mycobacteria (e.g., *M. tuberculosis* and *M leprae*) and hybridizing a probe. A probe that hybridizes to *M. tuberculosis* DNA but not to *M. leprae* DNA is, thus, *M. tuberculosis* specific.

It will be appreciated that in determining probe specificity and in utilizing the method of this invention to detect mycobacteria, a certain amount of background signal is typical and can easily be distinguished by one of skill from a specific signal (see discussion of probe "detection" below).

Other methods for determining specificity will be apparent to one of skill. For example, one of skill will realize that nucleic acid sequence information (e.g., available in computer databases such as GenBank, or otherwise determined) may help identify mycobacteria specific sequences. In addition, mycobacteria specific probes have been described by others (see, for example, WO 88/03957 and Edwards et al., *Nucleic Acid. Res.,* 17: 7843–7853 (1989)).

In one embodiment the probe can hybridize to the entire mycobacterial genomic DNA or to subsequences thereof. In a second embodiment, the probe hybridizes to mycobacterial rRNA (or rDNA) sequences. Particularly preferred probes comprise the total genomic mycobacterial DNA. It was a surprising discovery that the total genomic DNA of a Mycobacterium would specifically hybridize to mycobacteria while showing little or no cross-reactivity to nucleotide sequences from other prokaryotes or eukaryotes (see Example 6). While the genomic DNA from any mycobacterial species is suitable, it is particularly preferred to use as a probe DNA isolated from the mycobacterial species it is desirable to detect. Thus, where it is desired to detect MAC, DNA from *Mycobacterium avium* is preferred. Similarly, where it is desired to detect *Mycobacterium tuberculosis* a probe derived from *M. tuberculosis* is preferred. Mycobacterial cultures may be obtained from sources well known to those of skill in the art (e.g., American Type Culture, 12301 Parklawn Drive, Rockville, Md., 20852 USA). Isolation of total genomic DNA may be accomplished using routine methods known to those of skill (see, for example, Sambrook, supra., and the method of van Soolingen et al. *J. Clin Microbiol.* 29: 2578–2586 (1991) described in Example 1).

Numerous variations of steps used for hybridization to a sample comprising cells (i.e., in situ hybridization) are known in the art (see, e.g., Albertson *Genetics,* 1: 211–219 (1993) and Tijssen, J. *Hybridization with Nucleic Acid Probes* pp. 495–524, Elsevier, Amsterdam (1993) which are incorporated herein by reference) and can be applied in the instant method. Typically, the hybridization of the invention will include three steps: denaturation of the mycobacterial nucleic acid in the sample, hybridization of the probe to the sample, and rinsing (i.e., washing) away of unhybridized probe.

Denaturation: Where the target of probe hybridization is the mycobacterial DNA it is usual to denature the DNA prior to hybridization. (If the target is mycobacterial RNA this step may sometimes be omitted). Typically, denaturation is accomplished by exposure to heat sufficient to denature double-stranded DNA (e.g., 100° C. for 5 minutes). Denaturation can also be effected by certain organic compounds (e.g., formamide, tetramethylammonium chloride). Thus, in the presence of 70% formamide and 2×SSC, 5 minutes at 72° C. is sufficient. In addition to denaturation of the nucleic acids in the sample, if the probe is a double stranded DNA it too should also be denatured.

Hybridization: Hybridization temperature will typically be from 37° C. to 42° C., but can vary between about 30° C. and 50° C. In one embodiment, hybridization is at 37° C. in a solution containing denatured probe, 50% formamide and 2×SSC. In a second embodiment 10% (w/v) dextran sulfate is added to increase the rate of hybridization. Without being bound to a particular theory, it is believed that dextran occupies volume so that the effective concentration of the probe is increased which increases the rate (kinetics) of the hybridization.

Washing out of excess unbound material: Following hybridization the unannealed probe will be washed out. The wash step may vary from five minutes to an hour or more. One of skill in the art will appreciate that, in ex vivo hybridizations, such as Southerns or Dot Blots, it is typically the wash step that determines the stringency and facilitates dissociation of mismatched duplexes. In one embodiment the unannealed probe is removed by washing in 1×SSC at 70° C. for 5 minutes; 2×SSC at 37° C. for 5 minutes; 2×SSC at room temperature for 5 minutes, and $H_2O$ at room temperature for 5 minutes. In other embodiments the wash solutions may include other components such as formamide, buffers, or detergents.

E. Detecting the Hybridized Probe

It will be understood that the method of detection of hybridized probe will depend on the label used. According to the invention, the probe must be labeled so as to be detectable when hybridized to a sample. Methods for labeling nucleic acids are well known in the art and include direct detection methods (e.g., where the nucleic acid comprises or is covalently bound to a moiety that can be detected) and indirect (i.e., secondary) detection methods (e.g., where the nucleic acid is covalently bound to a moiety that can in turn be specifically bound by a detectable component). Detection methods include incorporation of a radioisotope, directly conjugated fluorophores, chemiluminescent agents (e.g., luciferin, 2,3-dihydrophthalazinediones (e.g., luminol)), enyzmes (e.g., alkaline phosphatase or horseradish peroxidase), enzyme substrates, and chromophores. As noted above detection methods also include detection through a ligand-antiligand complex (e.g., as when a nucleic acid probe is conjugated to biotin which, in turn, is bound by labeled avidin or streptaviden or when the probe is conjugated to digoxigenin and bound by labeled antidigoxigenin antibody). The methods employed in labeling are well known in the art and include methods described in Sambrook supra., and in Kessler, C. "Nonradioactive labeling Methods for Nucleic Acids" in *Nonisotopic DNA Probe Techniques,* Kricka, L., ed. pp. 29–92, Academic Press, San Diego 1992, both of which are incorporated herein by reference.

A preferred embodiment of the present invention is the use of a fluorescently-labeled nucleic acid probe. Hybridization of a fluorescently-labeled nucleic acid probe to a sample (i.e., fluorescent in situ hybridization (FISH)) has several advantages. For example, detection of hybridization by fluorescence allows the observer to view the hybridization signals in a cytologic and histologic context. The nuclei may be counterstained, and cytologic and/or histologic features appreciated. Furthermore, fluorescently-labeled nucleic acid probes are stable and relatively non-toxic and mycobacteria may be detected using a fluorescent microscope which is commonly found in clinical laboratories.

Fluorescent compounds include fluorescein and its derivatives, rhodamine and its derivatives, dansyl, umbelliferone, Texas Red, tetramethylrhodamine, Cy3, Cy5 and others. Nucleic acids may be enzymatically or chemically labeled with florescent compounds by a variety of methods as noted above. In one embodiment MTb genomic DNA is nick-translated in the presence of, e.g., fluorescein-12-dUTP. In a second embodiment, biotinylated nucleic acid probes are used, and hybrids are detected by fluorescein-avidin binding. In a third preferred embodiment, DNA probes are directly labeled with fluorophores. For example, the red/orange emission spectra "Spectrum Orange™" has been used to directly label purified total MTb genomic DNA according to the method of Imagenetics (Naperville, Ill.). An unexpected discovery of the present invention is that direct labeling results in a reduction of the background signal commonly encountered using fluorescein labeled secondary detection systems. Thus, while direct labeling is not critical to the practice of this invention, the use of direct labeled probes is preferred. However, the use of indirect labels would require a shorter portion of the preparation time in a low light environment and may therefore be more convenient.

In a preferred embodiment, a fluorescently labeled probe is used and a fluorescence microscope is used to examine the sample. The use of fluorescent microscopy is well known in the art. As appropriate, the microscope is equipped with a fluorescent (excitation) light source and with appropriate filters, e.g., to enhance counterstaining or reduce background or autofluorscence.

It will be appreciated that in determining probe specificity and in utilizing the method of this invention to detect mycobacteria, a certain amount of background signal is typical and can easily be distinguished by one of skill from a specific signal (see discussion below under "detection"). For example, when a fluorescently labeled probe is used, the signal is easily visualized, utilizing fluorescent microscopy, as a discrete light source substantially brighter (twice as bright or greater) than the general background and occurring with a typical morphology as described below. Detailed evaluation of the signal may be made in comparison to a cytological evaluation of the sample.

A DNA counterstain such as propidium iodide allows a cytologic evaluation of a specimen. With this, eukaryotic nuclei from the host and microorganisms can be evaluated for their frequency of occurrence and their morphology. Bacteria can be identified as either cocci or rods and these can be differentiated from fungi which are larger and of a differing morphology. Likewise fungi can be differentiated from the eukaryotic nuclei.

While the cytologic appearance of the specimen is being evaluated through the DNA counterstain, positive hybridization can be detected in a second color using a dual pass filter. Thus, a positively hybridized bacillus can be distinguished from a background signal because the hybridization signal is in the same location of a morphologically correct (rod-shaped for mycobacteria) bacillus identified from the DNA counterstain. For example, when a fluorescein-labeled DNA probe (green) and a propidium iodide counterstain is used, a green signal which does not correspond to a red counterstain signal can be discounted as a background signal. In addition, the hybridization signal should also have a similar size and morphology to the actual organisms. Thus, for mycobacteria, this signal should also have a rod shape approximately 0.2 to 0.5 μm in length. Finally, as most *Mycobacterium tuberculosis* is present intracellularly within macrophages, the positive signals should be found in clusters closely associated to a eukaryotic nucleus. Often a rim of residual cytoplasm is also present which encircles these clusters. Background signals are not observed in this pattern.

One of skill would recognize that certain artifacts are routinely disregarded when performing a histological evaluation. For example, autofluorescence, sample distortion and bright artifacts tend to occur around the edges of the tissue section. Thus putative signals in this region are typically disregarded as noise. Similarly signals outside the focal plane of the microscope are also ignored. In addition, when the hybridization is to DNA, background signals which are out of the plane of the nuclei/DNA are also ignored.

Although the steps of the method are typically carried out manually, the invention also provides for use of the method when one or more of the steps is automated. In particular, equipment is widely used in clinical histology laboratories to fix, wash, dehydrate and otherwise process samples. Because the method of this invention provides a high signal to noise ratio, detection methods can also easily be automated. For example, where a fluorescently labeled probe is used, a fluorescence microscope may be equipped with a video camera connected to a computer controlled data acquisition system. Numerous programs are available that provide image enhancement and feature detection (see, for example, SigmaScan™, Jandel Scientific, Sausalito, Calif.). Such systems will provide rapid screening and analysis of samples processed according to the methods of this invention.

Kits for the Detection of Mycobacteria

This invention also provides a kit that can be used for carrying out the method of detecting mycobacteria. The kit includes a instruction manual that teaches the method and describes use of the other components of the kit. The kit also includes at least one of the following components: a labeled nucleic acid probe capable of specific hybridization to a mycobacteria nucleic acid, a solution comprising formaldehyde, an organic solvent, a reducing agent, and a protease. Moreover, the kit can also include a "test sample" comprising a non-embedded animal cell having an intracellular mycobacterium fixed with a solution comprising formaldehyde. This test sample will be useful as a positive control for the method. The kit can also include a "second test sample" comprising a non-embedded animal cell having an intracellular mycobacterium processed according to the method of the invention and wherein a nucleic acid of the mycobacterium is hybridized to a labeled nucleic acid probe. The second test sample can also be used as a positive control for the detection of mycobacteria. Accordingly the invention also provides compositions comprising a non-embedded animal cell having an intracellular mycobacterium, wherein the cell is fixed with a solution comprising formaldehyde, and wherein a nucleic acid of the mycobacterium is or is not hybridized to a labeled nucleic acid probe.

EXAMPLES

The invention is illustrated by the following examples. These examples are offered by way of illustration, not by way of limitation.

Example 1

Detection of Mycobacterium in Human Sputum

A. Preparation of a Labeled Nucleic Acid Probe

Total mycobacterial genomic DNA was isolated from MTb (H37Rv strain, ATCC 27294) according to published procedures (van Soolingen et al. *J. Clin Microbiol.* 29: 2578–2586 (1991). Briefly, a 100 ml stationary culture was grown in Middlebrook 7H9 supplemented with 10% OAD (0.06% saponified oleic acid, 5% bovine albumin fraction V, 2% dextrose) and 0.1% Tween 80 for 3 weeks. Twenty four hours prior to harvesting, cultures were adjusted to 1 mg/ml d-cycloserine and 0.1 mg/ml ampicillin. Cultures were heat inactivated by incubation at 75° C. for 20 minutes, cells pelleted, and cell pellets resuspended in 500 μl TE (10 mM Tris, 1 mM EDTA, pH 8.0). Lysozyme was added to a final concentration of 1 mg/ml. The specimen was incubated at 37° C. for 1 hour, 70 μl of 10% SDS and 6 μl of 10 mg/ml proteinase K were added, followed by incubation for an additional 10 minutes at 65° C., and addition of 80 μl of 10% N-cetyl-N,N,N,-trimethyl ammonium bromide. The solution was vortexed briefly and then incubated for 10 minutes at 65° C. An equal volume of chloroform-isoamyl alcohol (24:1 v/v) was added, the solution was vortexed for 10 sec, and then centrifuged (10,000 xg) at room temperature for 5 minutes. The upper aqueous layer was removed, 0.6 volume of isopropanol was added and the sample was incubated for 30 minutes at −20° C. DNA was then pelleted by centrifugation (10,000X g, 15 minutes, 4° C.). The DNA pellet was washed once with 70% ethanol, air dried and redissolved in TE. Analysis of the purified DNA by standard 0.8% agarose gel electrophoresis revealed the DNA to be greater than 23 kb in size.

DNA concentration was determined using a standardized fluorometer and the probe was labeled with fluorescein-12-dUTP (Boehringer Mannheim Corp., Indianapolis, Ind.) by nick translation using the Bionick Labeling System (Gibco BRL, Gaithersburg, Md.). A dNTP mixture was made to replace the one in the bionick kit which did not contain biotin-labeled nucleotide or unlabeled dTTP. One μg of purified total genomic MTb DNA was incubated at 15° C. for 90 and the reaction was then stopped by heating at 75° C. for 10 minutes. Unincorporated nucleotides were eliminated using a Sephadex™ column and probe size was verified on a 1% agarose gel with most of the DNA probes ranging from 300–600 base pairs in length.

B. Hybridization and Detection of Mycobacterium Nucleic Acids

Three samples of sputum from human patients diagnosed with *Mycobacterium tuberculosis* infection were obtained from San Francisco General Hospital. Samples were sputum smears made onto glass slides and heat fixed (over a flame). Each sample was separately fixed in 10% neutral-buffered formalin (2400 ml of 37% formaldehyde, 80 g NaOH, 353 g $NaPO_4$ dissolved and diluted to a volume of 6400 ml) for 6 hours at room temperature. The samples were dehydrated for 10 minutes each in 70-, 85-, and 100% ethanol (EtOH), followed by immersion in xylene (Sigma, St. Louis, Mo.) for 10 minutes. After removal of the xylene by rinsing twice in 1×SSC (first for 10 minutes, then overnight) the samples were washed in 100% EtOH for 2×5 minutes and air-dried overnight.

The samples were treated for 10 minutes at 80° C. with 1M NaSCN (Sigma), washed 2×5 minutes in water, and heated dry. Pepsin (4 mg/ml in 0.2M HCl) was added at 4° C. and incubated at 4° C. for 5 minutes, followed by incubation at 37° C. for 5 minutes. The sample was then incubated for nine hours at room temperature in 70% formamide (Ultrapure, Gibco BRL, Gaithersburg, Md.), 0.1% (w/w) Tween20 (Polyoxyethylenesorbitan monolaurate, Sigma), 2×SSC. The samples were then overlaid with denaturing solution (70% formamide, 2×SSC) and incubated for 5 minutes at 72° C. The slides were blotted dry before addition of probe.

A hybridization mix prepared by combining 12 μl $H_2O$, 42 μl master mix #1 (5 ml formamide, 1 ml 2×SSC, 1 g dextran sulfate and X ml $dddH_2O$ to make a total volume of 7 ml, pH adjusted to 7.0) and 6 μl MTb-FITC probe (supra) was heated to 72° C. for 5 minutes and overlaid onto the samples. A coverslip was placed over the sample and sealed with rubber cement. The slide were placed in a plastic bag in a humid box and incubated at 37° C. overnight (approximately 16 hours) in a humidified environment.

Following the overnight incubation the coverslip was removed and the slide washed and dehydrated as follows: 1×SSC at 70° C. for 5 minutes; 2×SSC at 37° C. for 5 minutes; 2×SSC at room temperature for 5 minutes; $H_2O$ at room temperature for 5 minutes; 2 minutes each in 70-, 85-, and 100% EtOH at room temperature. The slides were dried at 37° C. Twenty μl of antifade (1% p-phenylenediamine hydrochloride (Sigma), 90% glycerol in PBS, pH 7.0) was added and the slide was coverslipped and sealed with clear nail polish.

The slides were examined using a Zeiss Axiophot fluorescence microscope equipped with a double-band pass filter (Chroma Technology, Brattleboro, Conn.) and a 63×NA 1.3 oil objective. This permitted simultaneous visualization of fluorescein (green) and propidium iodide (red). The propidium iodine counterstain (red) was used to identify and evaluate the morphology of all of the DNA containing material on the slide.

Rods and cocci were present diffusely on each of the three slides. Nuclei from human cells present in the specimen, fungal, bacterial microorganisms could be seen with the propidium iodide. Positive hybridization was identified by green fluorescence in a position over a simultaneously red-staining, rod-shaped organism. All three slides contained occasional single and clustered positive, green hybridization signals. The clusters were associated with human nuclei indicating that these organisms were located intracellularly in a pulmonary macrophage. Fewer single positive rod-shaped organisms were identified within all three specimens either intra- or extracellularly. Background green fluorescence was minimal and always easily differentiated from a hybridization signal because the background signal was either not in a rod morphology or was not associated with simultaneous red propidium iodide staining.

Example 2

Glutaraldehyde Fixation Does Not Allow Mycobacteria Detection

Acid fast bacilli (AFB) cultured in macrophages were prepared by standard means. Briefly macrophages (J774) cells were grown to a concentration of $1\times10^5$ cells/ml in DME supplemented with 5% newborn calf serum. To each well of a LabTek slide was added 0.5 ml of culture solution containing cells. Each well was then inoculated with 0.05 ml of a one week old culture of *Mycobacterium tuberculosis* (~1 McFarland or ~$2\times10^7$ bacteria/ml). The LabTek slide was incubated overnight at 37° C. in 5% $CO_2$. The old medium was removed and the slide washed with 0.5 ml of Hanks BSS. The slides were allowed to air dry in a hood under ultraviolet light. The chambers and gaskets were removed from the slides and the cells were heat fixed by flaming the slides for approximately 3 seconds.

The samples were then fixed with: (a) 2.5% buffered glutaraldehyde (2.5% glutaraldehyde buffered to pH 7.2 with sodium cacodylate) for 6 hours or with (b) 10% neutral buffered formalin for zero or 5 minutes, or 1, 3 or 6 hours, all at room temperature. The slides were then processed as in Example 1, except that the incubation with formamide/Tween20 was for 1 hour. Hybridization was performed as described in Example 1. Following hybridization, washing and dehydration, antifade containing propidium iodide was added to the samples, but was washed out (100% EtOH, 1×10 minutes plus 1×1 hour, both at 20° C.) after it was found to interfere with visualization at the concentration used.

The slides were examined as described in Experiment 1. All of the specimens which were fixed in formalin had a similar appearance which was markedly different from similar specimens fixed in gluteraldehyde. The macrophage nuclei in all of the glutaraldehyde-fixed specimens were highly autofluorescent, especially in the cytoplasm which did not appear to be digested away at all by the subsequent protease treatment. Very few rod-shaped organisms could be seen. None were visualized intracellularly within the cytoplasm and only an occasional one was observed extracellularly. In the few bacilli which could be visualized, no positive hybridization was detected. Thus, in contrast to the formalin fixation which allows subsequent hybridization, it appears that the glutaraldehyde fixation does not permit successful hybridization. Clearly, the macrophages were not digested by the pepsin treatment, and this made access to the majority of the mycobacterial bacilli difficult. Still, however, it appears that the actual mycobacterial wall was also not permeabilized as the extracellular bacilli also did not show hybridization.

Example 3

Heat and Acetone Fixation Does Not Allow Mycobacteria Detection

Slides were obtained from San Francisco General Hospital containing *Mycobacterium tuberculosis* smears, *Mycobacterium tuberculosis*-infected J cells and uninfected J cells all of which were either heat or acetone fixed. The slides were prepared as in Example 1 except the exposure to a formaldehyde solution was eliminated. Hybridization was performed with the Mycobacterium genus-specific 16S ribosomal RNA specific probe described in Example 5. Hybridization was performed as in Example 1, however the wash was 50% formamide, 2×SSC, 0.1% Tween 20 (3×15 minutes at 42° C.), then 2×SSC (2×10 minutes at 42° C.), then 0.1×SSC (1×10 minutes at 42° C.), then PN (0.05% NP40, 100 mM phosphate buffer, pH 8.0), then they were drained and counterstained with DAPI in antifade.

The rod-shaped mycobacteria and the nuclei of the macrophage J-cells were visible on the DAPI (blue) DNA counterstain, however, no positive (red) hybridization was seen. Thus, an extended xylene treatment on mycobacteria that have been both heat and acetone fixed does not permeabilize the membrane. The treatment was identical to that performed on sections of formalin-fixed, paraffin-embedded tissue where hybridization was successful (see Example 5). This suggests that the formalin treatment renders the mycobacterial wall permeable to the DNA probe.

Example 4

Detection of Cultured Mycobacteria

Glass slides were prepared with adherent mycobacteria or adherent macrophage containing intracellular mycobacteria. Briefly, slides were coated with preparations of either mycobacterial culture suspensions (MAC or MTb) or macrophage containing intracellular mycobacteria (either MAC or MTb, at a ratio of 5:1 of mycobacteria to J cells, in DME/5% bovine calf serum, incubated overnight at 30° C. in humidified atmosphere containing 5% $CO_2$). The old medium was removed, the samples washed with 0.5 ml Hands BSS and then the slides were allowed to air dry under ultraviolet light. Samples were affixed to the slides by flaming for approximately 3 seconds. The samples were then fixed in neutral buffered formalin for 6 hours at room temperature. The samples were then incubated for 20 minutes each in sequentially graded ethanol baths [70%, 80%, 95%, 100% (v/v) ethanol], and placed in 100% xylene at room temperature for 20 minutes, a fresh bath of 100% xylene for 3 hours, and a fresh bath of 100% xylene for 12 hours at 55° C. Slides were washed twice for 5 minutes per wash in 100% ethanol, heat dried at 60°–70° C., incubated in 1M NaSCN for 10 minutes at 80° C., washed twice in distilled deionized water at room temperature for 5 minutes per wash, dried at 60°–70° C., and cooled to 4° C. Slides were overlaid with a solution of 4 mg/ml pepsin in 0.2M HCl, incubated for 5 minutes at 4° C., warmed to 37° C. and incubated for an additional 5 minutes, then placed in 70% formalin/0.1% Tween 20 for 1 hour at room temperature.

The slides were drained, warmed to 70° C., and incubated in 70% formalin/2×SSC, pH 7 for 5 minutes at 72° C. to denature DNA. The slides were then cooled to 37° C. and blotted dry. The hybridization solution containing the labeled probe in a volume of 30 µl/slide was added, the slide coverslipped, the edges of the coverslip sealed with rubber cement, and incubated at 37° C. overnight. The following day, the rubber cement was removed and coverslips floated off in 1×SSC at room temperature. Slides were then warmed to 60°–70° C. and washed in 1×SSC for 5 minutes at 72° C., 2×SSC for 5 minutes at 37° C., 2×SSC for 5 minutes at room temperature, and distilled deionized water for 5 minutes at room temperature. Slides were subjected to sequential ethanol baths for 2 minute incubations in each bath (70%, 85%, 100% (v/v) ethanol) and dried completely at 37° C. Slides were then counterstained with propidium iodide (PI)/antifade (1% p-phenylenediamine hydrochloride (Sigma, St. Louis, Mo.), 90% glycerol in phosphate buffered saline, pH 7.0 with 0.1 µg/ml propidium iodide), coverslipped, edges of the coverslip sealed with rubber cement, and visualized on a fluorescent microscope.

Both the smeared mycobacteria and the cultured mycobacteria in macrophages showed high levels of hybridization (signal). Definite rod shapes were visible. There was better hybridization in areas where there was a high concentration of bacilli, but individually rods could be clearly seen as well. Mycobacteria were particularly visible in the cultured macrophages.

Example 5

Mycobacteria Detection in Embedded Material

A. Genus-Specific Probes

Mycobacterial genus-specific probes, each an oligonucleotide based on unique or shared mycobacterial 16S rRNA sequences, originally obtained from GenProbe, were directly fluorescently labelled and supplied by Imagenetics. The mycobacteria genus-specific probe is 34 base pairs in length (5'-ATCGCCCGCACGCTCACAGTTAAGCCGT-GAGATTC-3'), (SEQUENCE ID NO.:1) and spans nucleotide positions 595–628 of the *Mycobacterium avium* 16S rRNA and positions 559–592 of the MTb 16S rRNA.

B. Hybridization

A panel of 12 buffered formalin fixed paraffin embedded tissue specimens from various sources was screened for the presence of mycobacteria by the method of the invention. Seven of the specimens were obtained from individuals at risk for or infected with HIV-1. The sections were placed on slides and treated as follows: slides were heated for 10 minutes at 60°–65° C. on an incline, placed in 100% xylene at room temperature for 5 minutes, placed in 100% xylene at 56° C. for 15 minutes, placed in 100% ethanol at room temperature for 5 minutes, and placed on a 60°–65° C. heating plate for 1–2 minutes to evaporate the residual ethanol and bake the tissue onto the slide. Slides were then immersed in 1M NaSCN for 10 minutes at 80° C., rinsed twice for 5 minutes in distilled deionized water for 5 minutes/rinse at room temperature, and dried at 70°–80° C. Tissue was digested with pepsin (4 mg/ml in 0.2M HCl, 3–5 min. at 37° C.), rinsed for 5 minutes in deionized distilled water at room temperature, and blotted dry with a Kimwipe.

DNA was denatured by placing the slides in 70% formamide/2×SSC for 3 min at 73° C., slides were drained, dried with a Kimwipe, and kept at 37° C. until the addition of the hybridization solution. The hybridization solution containing probe was applied to the tissue (around which a rim of rubber cement had been made), slides placed in a plastic bag in a humid box, and incubated at 37° C. overnight. The slides were washed 3 times for 15 minutes each with 50% formamide/2×SSC, pH 7, at 42° C., then rinsed twice for 10 minutes each with 2×SSC at 42° C., washed 10 minutes with 0.05% NP40/100 mM phosphate buffer, pH 8 (PN buffer) at room temperature, and subjected to graded ethanol dehydration baths (ie., 70%/80%/100% ethanol with 10 minute incubations at each concentration). Residual ethanol was evaporated by placing slides on a 37° C. slide warmer, antifade containing 0.4 µM DAP1 added, and slides coverslipped and sealed with clear nail polish.

The hybridized specimen was examined with a Zeiss Axioscop equipped with multiple single and dual band pass filters. A dual band pass filter which allowed visualization of blue (DAP1 counterstain) and red (Spectrum Orange mycobacterium species specific probe signal) emission spectra was obtained from Imagenetics and used for evaluation of slides; this filter markedly reduced red spectrum autofluorescence and enhanced the Spectrum Orange signals. Slides were scanned using 10× oculars and a 40× objective (400× magnification) as this was the lowest power objective available, and positive hybridization was confirmed using a 63× or 100× objective (630× or 1000× magnification).

A bright fluorescent signal (FISH) was noted within 2 minutes of examination with 400× magnification. The positive signal was further evaluated on 1000× magnification; the hybridizing probe appeared to be localized to the cytoplasm of macrophages wherein numerous round structures, approximately 1 µm in diameter, were observed. Further microscopic examination revealed additional macrophages of similar appearance in this tissue section.

The results using the mycobacterial genus-specific probe, compared with conventional acid fast stain and culture results (when available) are shown in Table I.

Two specimens (#11 and 12) were notable for containing significant numbers of FISH positive signals either out of the plane of the tissue section or in the plane of the tissue section but localized to the edges. These represent "floaters," i.e., cross-contaminating mycobacteria present in the water baths used to generate sections from paraffin blocks. These mycobacteria may have been liberated from tissue blocks containing numerous amounts of mycobacteria during the sectioning process, leading to cross-contamination of tissue blocks processed next.

A positive FISH result was obtained for the 4 specimens (#1–4) for which mycobacteria were recovered by microbiological culture; only 3 of these 4 specimens (i.e., #1,3,4) had AFB detected on examination of an acid fast stain. A single specimen (#5) had an isolated positive FISH result in the absence of evaluation by AFB stain or microbiological culture. The possibility of a false positive FISH result in this case can not be excluded; given the eventual development of mycobacterial infection in this HIV-1 infected patient, however, it is also possible that the positive FISH result may have been a true positive result. Of note, there was no cross-hybridization of the mycobacteria genus-specific probe with the abundant cryptococcus present in this specimen.

TABLE 1

| Spec. # | AFB stain result[1] | FISH result[2] | Tissue source; Comments | Microbiology Laboratory Result |
|---|---|---|---|---|
| 1 | ++++ | + | Lymph node; caseating granulomas present. | MTb recovered from same specimen. |
| 2 | negative | + | Lymph node; necrotizing granulomas present; parallel specimen sent to the Microbiology Laboratory had AFB detected. | MTb recovered from same specimen. |
| 3[3] | ++++ | + | Liver biopsy; foamy macrophages containing AFB present. | MAC recovered from same specimen. |
| 4[3] | ++++ | + | Bone marrow clot and biopsy; granulomata present. | MAC recovered from same specimen. |
| 5[3] | ND | + | Transbronchial biopsy; cryptococcus detected; AFB present in duodenal biopsy obtained 17 months later. | No culture of specimen obtained; no recovery of mycobacteria from blood cultures obtained at the same time. |
| 6[3] | ND | negative | Pyogenic granuloma | No culture of specimen obtained. |
| 8 | ND | negative | Appendix; intense neutrophilic infiltrate present. | Coagulase negative Staphylococcus recovered from culture of specimen. |
| 9[3] | negative | negative | Rectal biopsy; intracytoplasmic and intranuclear cytomegalovirus-like inclusions present. | No mycobacteria recovered from 3 independent blood cultures obtained at the same time. |
| 10 | ND | negative | Orbital abscess; Gram negative rods present. | No culture obtained. |
| 11[3] | negative | negative* | Small bowel, esophageal and | No mycobacteria or fungi recovered |

TABLE 1-continued

| Spec. # | AFB stain result[1] | FISH result[2] | Tissue source; Comments | Microbiology Laboratory Result |
|---|---|---|---|---|
| | | | rectal biopsies; intracytoplasmic and intranuclear cytomegalovirus-like inclusions present; same sites biopsied 5 months later with no AFB detected. | from 2 independent blood cultures obtained at the same time; Isospora detected in stool. |
| 12[3] | negative | negative* | Bone marrow biopsy and clot; poorly formed non-caseating granulomas containing macrophages with intracytoplasmic yeasts resembling Histoplasma present. | *Histoplasma capsulatum*, but not mycobacteria, were recovered from culture of the same specimen. |

[1]Acid fast stain (Kinyoun or Fite). +++: numerous AFB present. +: at least a single AFB present displaying characteristic beaded rod morphology.
[2]A positive FISH result was defined as observed one or more cells containing intracytoplasmic inclusions.
[3]Specimens obtained from individuals at risk for or infected with HIV-1.
ND = not done.
*denotes specimens where FISH signals of the correct color but not in the plane of the tissue section were observed (ie., "floaters").

A negative FISH result was observed for 7 specimens (#6–12). Of note, no cross hybridization (i.e., false positive) of the mycobacterial genus-specific FISH probe was observed with these 7 specimens, where either bacteria [i.e., direct detection of Gram positive cocci and Gram negative rods in specimens #6 and #10, presumed presence of bacteria in 1 pyogenic granuloma and in a inflamed appendix (specimens #7 and #8), and probably numerous bacteria present in the 2 specimens consisting of biopsies obtained from the gastrointestinal tract (specimens #9 and #11)] or fungi (i.e., *Histoplasma capsulatum* in specimen #12) were present. This data provides evidence that there is no apparent cross-reactivity of the mycobacteria genus-specific probe with Staphylococcus sp. (present in specimen #8), Enterobacteriaceae (presumably present in specimen #8), or Cryptococcus and Histoplasma spp. (specimens #5 and #12).

All slides were stored at 4° C. after FISH was performed. Fluorescent microscopic evaluation of the FISH+ slides 3–6 months after hybridization revealed little if any diminution in fluorescent signal. This study demonstrates that the mycobacterial genus-specific FISH probe, as compared to traditional AFB stains, had increased sensitivity and comparable specificity.

Example 6

A Total Genomic DNA Probe is Specific for Mycobacteria

Culture plates with the following microorganisms were obtained from the clinical microbiology laboratories at the San Francisco General Hospital: *Staphylococcus aureau*, Group A Streptococcus, *Streptoccus pneumoniae*, α-Streptococcus, *Serratia marcescens, Proteus vulgaris, Enterobacteriacea coli* and *Pseudomonas aeruginosa.* All bacteria were isolated from clinical samples and were definitively identified. Bacteria were scraped from the culture plates and suspended in 10 ml of phosphate buffered saline (PBS) which was then vortexed until the solution was turbid and homogeneous. The bacteria were pelleted and washed again in PBS. Next, 0.3 ml of the solution was removed and mixed with 0.7 ml of absouted ethanol:glacial acetic acid 3:1 which was mixed immediately and stored 7 days at 4° C. The bacteria were then dropped onto slides and allowed to dry 10 hours at room temperature. A heat-fixed control slide of *Mycobacterium tuberculosis*-infected J cells was included in this experiment as a positive control.

The slides were fixed in neutral buffered formalin for 6 hours at room temperature, incubated for 20 minutes each in sequentially graded ethanol baths [70%, 80%, 95%, 100% (v/v) ethanol], and placed in 100% xylene at room temperature for 20 minutes, a fresh bath of 100% xylene for 3 hours, and a fresh bath of 100% xylene for 12 hours at 55° C. Slides were washed twice for 5 minutes per wash in 100% ethanol, heat dried at 60°–70° C., incubated in 1M NaSCN for 10 minutes at 80° C., washed twice in distilled deionized water at room temperature for 5 minutes per wash, dried at 60°–70° C., and cooled to 4° C. Slides were overlaid with a solution of 4 mg/ml pepsin in 0.2M HCl, incubated for 5 minutes at 4° C., warmed to 37° C. and incubated for an additional 5 minutes, then placed in 70% formalin/0.1% Tween 20 for 1 hour at room temperature. Hybridization and wash steps were performed as in Example 4.

The control slide showed positive, green hybridization of the mycobacteria, both intracellularly and extracellularly. In contrast, no positive hybridization was identified on any of the 8 non-mycobacterial samples tested. While some slides contained higher concentrations of bacteria than others, each contained regions with enough organisms for evaluation. This experiment confirms that DNA probe generated from the entire genome of *Mycobacterium tuberculosis* does have a high specificity, especially against the 8 organisms tested here which represent the most common aerobic bacteria present in clinical sputum samples.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

and then treated with the protease at about between 15° C. and 60° C.

---

---

What is claimed is:

1. A method for detecting mycobacteria in a sample comprising non-embedded animal cells or non-embedded bacteria, said method comprising the steps of:
   a) contacting the sample with a solution comprising formaldehyde;
   b) contacting the sample with an organic solvent selected from the group consisting of xylene, benzene, hexane, toluene, heptane, octane, acetone and acetonitrile;
   c) contacting the sample with a protein-degrading agent which is a protease;
   d) hybridizing a labeled nucleic acid probe to the sample, wherein the probe specifically hybridizes to a Mycobacterium nucleic acid; and
   e) detecting the hybridized probe, wherein hybridized probe is indicative of the presence of mycobacteria in the sample.

2. The method of claim 1 wherein the sample is selected from the group consisting of: sputum, blood, blood cells, a tissue biopsy sample, and pleural fluid.

3. The method of claim 2 wherein the sample is sputum.

4. The method of claim 1 wherein the animal cells are mammalian cells.

5. The method of claim 4 wherein the mammalian cells are human cells.

6. The method of claim 5 wherein the mammalian cells are macrophages or macrophage-type cells.

7. The method of claim 6 wherein the animal cells are selected from the group consisting of: U937 cells and murine J cells.

8. The method of claim 1 wherein the mycobacteria are *Mycobacterium tuberculosis* or *Mycobacterium avium* complex.

9. The method of claim 1 wherein the mycobacteria are intracellular.

10. The method of claim 1 wherein the solution comprising formaldehyde is neutral-buffered formalin.

11. The method of claim 1, wherein the protease is selected from the group consisting of: pepsin, pronase, lysozyme, trypsin, chymotrypsin, and proteinase K.

12. The method of claim 1 wherein the sample is first treated with the protease at about between 0° C. and 10° C.

13. The method of claim 1 wherein the sample is treated with a reducing agent before protease treatment.

14. The method of claim 13 wherein the reducing agent is sodium thiocyanate or guanidine thiocyanate.

15. The method of claim 1 wherein the nucleic acid probe is greater than 100 bases long.

16. The method of claim 15 wherein the nucleic acid probe comprises the total genomic DNA of a Mycobacterium.

17. The method of claim 1 wherein the nucleic acid probe is labeled with a label selected from the group consisting of an enzyme, a radioisotope, biotin, digoxigenin, and a fluorophore.

18. The method of claim 17 wherein the nucleic acid probe is labeled with a fluorophore.

19. The method of claim 1 wherein the nucleic acid probe is detected using a fluorescence microscope.

20. The method of claim 1 wherein the Mycobacterium nucleic acid is DNA.

21. A composition comprising a non-embedded animal cell having an intracellular Mycobacterium, wherein the cell is fixed with a solution comprising formaldehyde a protein-degrading agent which is a protease, an organic solvent selected from the group consisting of xylene, benzene, hexane, toluene, heptane, octane, acetone and acetonitrile, and wherein a nucleic acid of the Mycobacterium is hybridized to a labeled nucleic acid probe.

22. The composition of claim 21 wherein the mycobacterium is of the species *Mycobacterium tuberculosis* or *Mycobacterium avium* complex.

23. The composition of claim 21 wherein the labeled nucleic acid probe is labeled with a fluorophore.

24. A kit for clinical detection of mycobacteria in animal cells comprising an instruction manual describing a method for detecting mycobacteria in a sample comprising non-embedded animal cells or non-embedded bacteria, said method comprising the steps:
   a) contacting the sample with a solution comprising formaldehyde;
   b) contacting the sample with an organic solvent selected from the group consisting of xylene, benzene, hexane toluene, heptane, octane, acetone and acetonitrile;

c) contacting the sample with a protein-degrading agent which is a protease;

d) hybridizing a labeled nucleic acid probe to the sample, wherein the probe specifically hybridizes to a Mycobacterium nucleic acid; and e) detecting the hybridized probe, wherein hybridized probe is indicative of the presence of mycobacteria in the sample;

wherein the kit further comprises a container containing a labeled nucleic acid probe capable of specific hybridization to a mycobacteria nucleic acid.

25. The kit of claim 24 further comprising a test sample comprising a non-embedded animal cell having an intracellular mycobacterium, wherein the cell has been fixed with a solution comprising formaldehyde and wherein a nucleic acid of the Mycobacterium is hybridized to a labeled nucleic acid probe.

26. The kit of claim 24 further comprising at least one container containing a component selected from the group consisting of: a labeled nucleic acid probe, a solution comprising formaldehyde, an organic solvent selected from the group consisting of xylene, benzene, hexane, toluene, heptane, octane, acetone and acetonitrile, a reducing agent, and a protease.

27. The kit of claim 26 wherein said container contains a nucleic acid probe.

28. The kit of claim 27 wherein said nucleic acid probe comprises the total genomic DNA of a Mycobacterium.

29. The method of claim 1 wherein the an organic solvent is selected from the group consisting of xylene, benzene, and hexane.

30. The method of claim 29, wherein said protease is selected from the group consisting of: pepsin, pronase, lysozyme, trypsin, chymotrypsin, and proteinase K.

31. The method of claim 30, wherein said organic solvent is xylene;

said protease is pepsin; and said nucleic acid is labeled with a fluorophore.

* * * * *